United States Patent [19]

Bonfield et al.

[11] Patent Number: 5,017,627
[45] Date of Patent: May 21, 1991

[54] COMPOSITE MATERIAL FOR USE IN ORTHOPAEDICS

[75] Inventors: William Bonfield, Welwyn; Jeremy A. Bowman, Iver, both of England; Marc D. Grynpas, Newton, Mass.

[73] Assignee: National Research Development Corporation, United Kingdom

[21] Appl. No.: 191,738

[22] Filed: May 2, 1988

Related U.S. Application Data

[63] Continuation of Ser. No. 721,135, Sep. 30, 1985, abandoned, which is a continuation of Ser. No. 637,692, Aug. 6, 1984, abandoned, which is a continuation of Ser. No. 250,664, Apr. 3, 1981, abandoned.

[30] Foreign Application Priority Data

Oct. 9, 1980 [GB] United Kingdom ............... 8032647

[51] Int. Cl.$^5$ ........................... A61F 2/00; C08K 3/32; C08L 23/00
[52] U.S. Cl. .................................. 523/115; 524/414; 524/417; 524/586; 623/16; 623/22
[58] Field of Search .................. 623/16, 22; 523/115; 524/414, 586, 417

[56] References Cited

U.S. PATENT DOCUMENTS

| | | | |
|---|---|---|---|
| 4,055,862 | 11/1977 | Farling | 3/1.91 |
| 4,104,289 | 8/1978 | Jones | 524/586 |
| 4,131,597 | 12/1978 | Blüethgen et al. | 523/115 |
| 4,178,686 | 12/1979 | Riess et al. | 433/201 |
| 4,192,021 | 3/1980 | Deibig et al. | 3/1.9 |
| 4,202,055 | 5/1980 | Reiner et al. | 3/1.91 |
| 4,548,959 | 10/1985 | Nagai et al. | 623/16 |

FOREIGN PATENT DOCUMENTS

| | | | |
|---|---|---|---|
| 0011528 | 5/1980 | European Pat. Off. | |
| 1234986 | 2/1967 | Fed. Rep. of Germany | 524/586 |
| 1044028 | 9/1966 | United Kingdom | |
| 1073804 | 6/1967 | United Kingdom | |
| 1115925 | 6/1968 | United Kingdom | |
| 1172629 | 12/1969 | United Kingdom | |
| 1362912 | 8/1974 | United Kingdom | |
| 1409508 | 10/1975 | United Kingdom | |
| 1470124 | 4/1977 | United Kingdom | |
| 1540624 | 2/1979 | United Kingdom | |
| 1562952 | 3/1980 | United Kingdom | |
| 2031450 | 4/1980 | United Kingdom | |

OTHER PUBLICATIONS

Prostheses and Tissue: The Interface Problem; National Institute of Dental Research-Office of Naval Research 5th Annual Biomaterials Symp. 4/1973.
Chemical Abstracts vol. 76:154949x (1972).
Chemical Abstracts vol. 84:35296n (1976).
Prosthetics, "Materials for the Replacement of Osteoarthritic Hip Joints", by W. Bonfield, pp. 712-716.
Shell Polymers 9, 3(1985), "Composites for Bone Replacement", W. Bonfield, Department of Materials, Queen Mary College, London.
Plastics and Rubber Processing and Applications vol. 4, No. 3, 1984, "The Influence of Compounding Route on the Mechanical Properties of Highly Loaded Particulate Filled Polyethylene Composites", pp. 261-269.
Elsevier Science Publishers B. V., Amsterdam, 1986, "In Vivo Evaluation of Hydroxyapatite Reinforced Polyethylene Composites", pp. 153-158.

Primary Examiner—Paul R. Michl
Assistant Examiner—Thomas McDonald, Jr.
Attorney, Agent, or Firm—Finnegan, Henderson, Farabow, Garrett & Dunner

[57] ABSTRACT

A composite of a homo- or co-polyolefin having an average molecular weight greater than 100,000 with from 30 to 50% by volume of a particulate inorganic solid for use in endoprosthesis.

19 Claims, 1 Drawing Sheet

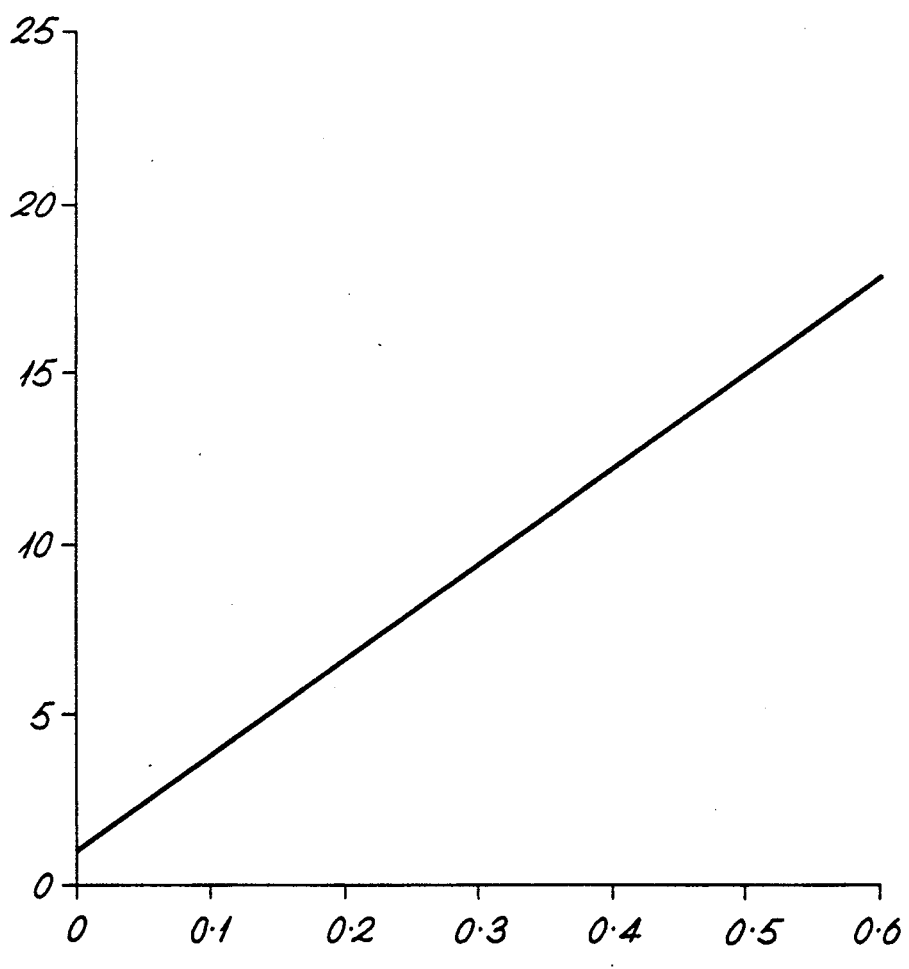

COMPOSITE MATERIAL FOR USE IN ORTHOPAEDICS

This application is a continuation of application Ser. No. 721,135, filed Sept. 30, 1985, now abandoned, which is a continuation of application Ser. No. 637,692, filed Aug. 6, 1984, now abandoned, which is a continuation of application Ser. No. 250,664, filed Apr. 3, 1981, now abandoned.

This invention relates to composite materials; more particularly, this invention relates to composite materials for use in orthopaedics, to processes for preparing the composite materials, and to prostheses incorporating them.

This invention relates principally, but not exclusively, to prosthesis, especially endoprosthesis; that is, to the artificial replacement of parts of the anatomy internally resident in the human or animal body, principally bone.

Animal bone and ivory have, in the past, been employed in orthopaedic prosthesis. As with all natural materials, however, it is difficult to ensure the supply of these materials with adequate and predictable mechanical strengths. Moreover, since they comprise protein which is not of the patient's origin inflammatory reactions may arise because of their biological incompatibility. Accordingly, surgeons have resorted, and still resort, to a variety of synthetic engineering materials whose envisaged uses were usually remote from prosthesis.

One major example is in total hip replacement: in general, the femoral head is replaced with a cast alloy, usually an austenitic stainless steel or Co-Cr alloy, secured, usually by a polymethylmethacrylate bone cement, in the marrow cavity and seated in a high density polyethylene acetabular cup. The alloys used are selected primarily by virtue of their biocompatibility, resistance to corrosion, adequate fracture toughness and fatigue strength. They have proved satisfactory, but less than ideal, in such applications; as a result, attention has recently been devoted to the development of even more "bioinert" prosthetic materials with comparable strength properties. Examples include titanium alloys and ceramics, principally alumina. The brittle nature of ceramics, however, presents new problems for prosthesis.

All such synthetic prosthetic materials hitherto used, however, suffer from one major defect: the prosthetic material eventually becomes detached from the bone to which it was originally affixed. That is, hitherto, major surgical prosthetic operations have been intrinsically impermanent.

The present invention seeks to provide composite materials suitable for use in orthopaedics, especially as endoprosthetic materials, which, in vivo, do not become detached from bone to which they are affixed.

According, therefore, to one aspect of the present invention there is provided a composite of a homo- or co-polyolefin having a weight average molecular weight ($\overline{M}_w$) greater than 20,000 with up to 80% by volume of a particulate inorganic solid. Preferably, the polyolefin comprises polyethylene, polypropylene, polybutylene or a copolymer of ethylene and at least one of propylene, butylene and hexene, preferably linear polyethylene.

It is desirable that the polyolefin has a weight average molecular weight ($\overline{M}_w$) greater than 20,000, suitably greater than 100,000, preferably greater than 300,000: below a $\overline{M}_w$ of 20,000 the polyolefin may not have a desirable level of biocompatibility. Desirably, the polyolefin has a $\overline{M}_w$ below 3,000,000, preferably below 1,000,000: above a $\overline{M}_w$ of 3,000,000 there are processing difficulties associated with forming and fabricating the composite.

The composite should desirably have no more than 80%, preferably from 10 to 70%, especially from 20 to 60%, by volume of the particular inorganic solid: above that value it is found that the particulate inorganic solid cannot be distributed homogeneously whereas at very low loadings the composite may be too compliant. The particulate inorganic solid component of the composite is present both to reinforce the composite and to enhance its stiffness, and is particularly suitable if its Young's modulus is from 50 to 150 GPa, preferably from 60 to 120 GPa. Suitable such inorganic solids are usually non-metallic and include ceramics, preferably calcium salts, for example calcium phosphates wherein the Ca:P ratio is from 1.0 to 1.5. Preferably, the calcium salt is a natural or synthetic hydroxyapatite or fluorapatite having a Ca:P ratio from 1.51 1.7. Other particulate inorganic solids include chalk, fly ash and silica.

The particulate inorganic solid, especially hydroxyapatite, may be used in the form of ground spherical particles, preferably wherein the particle size is from 90% being less than 100 $\mu$m to 0.05 $\mu$m, preferably from 90% being less than 50 $\mu$m to 0.1 $\mu$m. The inorganic solid may also be used in the form of acicular particles or platelets, the latter preferably having a maximum length of 500 $\mu$m and a maximum thickness of 20 $\mu$m. Mixtures of differing particulate inorganic solids may be used.

The composites in accordance with the present invention may be prepared by milling the polyolefin, suitably at a temperature above the softening point, for example for 200° to 260° C., preferably from 200° to 240° C., with the particulate inorganic solid which, desirably, has previously been dried, for example by heating at a temperature from 100° to 160° C. for a period of 3 to 12 hours. If necessary, the inorganic solid is first ground to the requisite particle size. The polyolefin is usually incorporated first in the mill, the inorganic solid being added in small quantities until the desired volume fraction is attained. The milling time will depend on the charge incorporated but for 0.5 kg is typically from 1 to 2 hours. For higher volume fractions of inorganic solid it is often more convenient to use a two-stage milling adding, say, the inorganic solid to produce a 40% volume fraction "hide"; cooling this; remelting on the mill; and adding the remainder of the inorganic solid.

It is also possible to produce a composite by mixing in an extruder, and, again, re-extruding to obtain higher volume fractions of inorganic solid is often more convenient. A further method of producing the composite is by comminuting and finely admixing the components in the solid phase; sintering the mixture; and compacting, as by isostatic pressing, the sintered product.

The composites according to this invention have a Young's modulus from 2 to 40, preferably from 10 to 30 GPa; that is, they have a Young's modulus in the range of values recorded for compact bone. The composites may be oriented in a machine direction, but it is preferred that the ratio $E_{\parallel}:E_{\perp}$ does not exceed 3, preferably 2.

By "Young's modulus" is meant herein the dynamic modulus measured ultrasonically by the method of Bonfield and Grynpas in "Nature", 270, No. 5636, pp. 453–454 (1977).

In accordance with a further aspect of this invention there is provided a composite of a homo- or co-polyolefin with a particulate inorganic solid for use in surgery as a prosthesis, especially where the composite is as hereinabove defined; and a prosthesis prepared from such a composite, preferably an endoprosthesis, particularly for the direct engagement of bone, which may be a fracture fixation device, a jaw prosthesis or a prosthesis for the simple substitution of a local section of bone; especially, however, the endoprosthesis is a bone joint device, particularly for partial or total replacement of the hip or knee joints. In particular, the composite may be used to fabricate either or both of the femoral head and stem and the acetabular cup into which the head seats in vivo, although it may be used in the prosthesis of any joint affected by arthrosis.

The prosthesis may be fabricated by compression or injection moulding. In the former, the solid composite is remelted, suitably at a temperature from 190° to 250° C., preferably 200° to 230° C., charged to the prosthesis mould cavity under load until the cavity is filled, and then cooled under load. In the case of injection moulding, similar temperatures are used, but care must be taken to use an injection pressure and speed below that which causes degradation by scorching.

It will often prove desirable, especially with a polyolefin with a $\overline{M}_w < 500,000$, to $\gamma$-irradiate the fabricated implant prosthesis. Not only will this give better resistance to creep and environmental stress cracking, but it will also sterilise the prosthesis.

Where processing difficulties are encountered or might be expected, it is often desirable to use a polyolefin of lower $\overline{M}_w$ to form the composite more readily and then to irradiate. Throughout the specification and claims, molecular weights and particle sizes refer to these parameters as charged; these may change during blending and fabrication.

This invention further provides a method of orthopaedic endoprosthesis for the animal or human body which comprises Preparing at least one bone stump to receive the prosthesis and engaging prosthesis as hereinabove defined to the or each bone stump.

The following Example illustrates the invention.

Polyolefin, as specified in Table I below, is melted and contained on and in the nip of a two roll mill. To the molten polyolefin are added aliquots of the inorganic particulate solid until the requisite volume fraction, as specified in Table I, is attached.

TABLE I

| | POLYOLEFIN (a) | MILL TEMP. (°C.) | MILLING TIME (hr.) | INORGANIC PARTICULATE SOLID (b) | RATIO (a:b) | | QUALITY PREPARED (g) |
|---|---|---|---|---|---|---|---|
| 1. | H020-54P[1] | 220 | 1 | $CaCO_3$ | 1:3 | by wt. | 200 |
| 2. | " | " | " | " | 1:1 | " | 100 |
| 3. | " | " | " | " | 1:2 | " | 150 |
| 4. | " | " | " | " | 1:3 | " | 200 |
| 5. | " | 225 | " | CBA[2] | 2:1 | " | 300 |
| 6. | " | " | " | " | 1:1 | " | 300 |
| 7. | " | " | " | " | 1:2 | " | 300 |
| 8. | " | 230 | 1.5 | " | 3:2[3] | by vol. | 450 |
| 9. | " | " | " | " | 2:3 | " | 500 |
| 10. | " | " | " | " | 1:4 | " | 500 |
| 11. | H060-45P[4] | 250 | " | HAP[5] | 1:9 | " | 500 |
| 12. | " | " | " | " | 1:4 | " | 400 |
| 13. | " | " | " | " | 1:3 | " | 340 |
| 14. | " | " | " | " | 1:3 | " | 550 |
| 15. | " | " | " | " | 2:3 | " | 230 |

[1] A linear polyethylene (ex. BP Chemicals Ltd.) having an MFI 0.05, $\overline{M}_n$ 33,000 and $\overline{M}_w$ 312,000.
[2] Calcined bone ash (ex. Podmore) which is dried (6 hours at 140° C.) and ground to nearly spherical particles of sub-micron size before adding to the polyolefin.
[3] Assuming a density of 3160 kg. m$^{-3}$.
[4] A linear ethylene hexene −1 copolymer (ex. BP Chemicals Ltd.) having a $\overline{M}_w$ about 240,000 with about 1–4 butyl branches per 1,000 chain carbon atoms.
[5] Synthetic hydroxyapatite in platelet form which is dried (8 hours at 140° C.) before adding to the polyolefin.

TABLE II

| | POLYOLEFIN (a) | INORGANIC PARTICULATE SOLID (b) | RATIO (a:b) | | PLAQUE WEIGHT (g) | DENSITY (kgm$^{-3}$) | PRESS TEMPERATURE (°C.) |
|---|---|---|---|---|---|---|---|
| 16. | H020-54P | $CaCO_3$ | 1:3 | by wt. | 17.4 | 1810 | 210 |
| 17. | " | CBA | 2:1 | " | 11.0 | 1150 | " |
| 18. | " | " | 2:1 | " | 11.0 | 1150 | " |
| 19. | " | " | 1:1 | " | 13.1 | 1360 | 210 |
| 20. | " | " | 1:1 | " | 13.1 | 1360 | " |
| 21. | " | " | 1:1 | " | 12.7 | 1320 | " |
| 22. | " | " | 1:1 | " | 12.5 | 1300 | 200 |
| 23. | " | " | 1:1 | " | 12.7 | 1320 | " |
| 24. | " | " | 1:1 | " | 12.7 | 1320 | " |
| 25. | " | " | 1:2 | " | 18.0 | 1870 | 220 |
| 26. | " | " | 1:2 | " | 16.5 | 1720 | " |
| 27. | " | " | 1:1 | " | 13.0 | 1360 | " |
| 28. | " | " | 1:2 | " | 16.5 | 1720 | " |
| 29. | " | " | 1:2 | " | 16.6 | 1730 | " |
| 30. | " | " | 1:2 | " | 16.4 | 1710 | 210 |
| 31. | " | " | 1:2 | " | 16.3 | 1700 | " |
| 32. | " | " | 4:1 | by vol | 13.7 | 1430 | 200 |
| 33. | " | " | 4:1 | " | 13.7 | 1430 | " |
| 34. | " | " | 4:1 | " | 13.3 | 1390 | " |

TABLE II-continued

| | POLYOLEFIN (a) | INORGANIC PARTICULATE SOLID (b) | RATIO (a:b) | | PLAQUE WEIGHT (g) | DENSITY (kgm$^{-3}$) | PRESS TEMPERATURE (°C.) |
|---|---|---|---|---|---|---|---|
| 35. | " | " | 4:1 | " | 13.0 | 1350 | " |
| 36. | " | " | 3:2 | " | 19.9 | 2070 | " |
| 37. | " | " | 3:2 | " | 19.6 | 2040 | " |
| 38. | " | " | 3:2 | " | 19.3 | 2010 | " |
| 39. | " | " | 2:3 | " | 26.8 | 2790 | " |
| 40. | " | " | 2:3 | " | 25.0 | 2600 | " |
| 41. | " | " | 2:3 | " | 25.2 | 2660 | " |
| 42. | H060-45P | HAP | 9:1 | " | 15.5 | 1610 | " |
| 43. | " | " | 9:1 | " | 15.0 | 1560 | " |
| 44. | " | " | 4:1 | " | 14.1 | 1470 | " |
| 45. | " | " | 4:1 | " | 14.9 | 1550 | " |
| 46. | " | " | 3:2 | " | 20.0 | 2080 | " |
| 47. | " | " | 3:2 | " | 18.4 | 1920 | " |

Further blends (see Table II) were made essentially as specified above. These were then compression moulded into plaques for use in determining mechanical properties of the blends.

In the accompanying drawing there is shown a graph depicting the relationship between Young's modulus, measured in GPa, as ordinate and the volume fraction of particulate inorganic solid. The blends used were 11 to 15 inclusive shown in Table I.

We claim:

1. A prosthesis for replacement of bone comprising a composite formed by compounding, in the solid phase, a homo- or copolyolefin having a weight average molecular weight ($M_w$) greater than 100,000 with from 30 to 50 percent by volume of a particulate calcium phosphate filler, said composite having a Young's modulus in the range of values recorded for compact bone.

2. A prosthesis according to claim 1 wherein the polyolefin comprises polyethylene, polypropylene, polybutylene, or a copolymer of ethylene and at least one of propylene, butylene and hexane.

3. A prosthesis according to claim 2 wherein the polyolefin comprises linear polyethylene.

4. A prosthesis according to claim 2 wherein the polyolefin has an $\overline{M}_w$ greater than 100,000 but less than 1,000,000.

5. A prosthesis according to claim 2 wherein the particulate calcium phosphate has a Young's modulus from 50 to 150 GPa.

6. A prosthesis according to claim 5 wherein the particulate calcium phosphate has a Young's modulus from 60 to 120 GPa.

7. A prosthesis according to claim 1 wherein the calcium phosphate has a Ca:P ratio from 1.0 to 1.5.

8. A prosthesis according to claim 2 wherein the inorganic solid is in the form of ground spherical particles.

9. A prosthesis according to claim 8 wherein the particles size is from 90% being less than 100 μm to 0.05 μm.

10. A prosthesis according to claim 2 wherein the inorganic solid is in the form of acicular particles or platelets.

11. A prosthesis according to claim 10 wherein the platelets have a maximum length of 500 μm and a maximum thickness of 20 μm.

12. A prosthesis according to claim 2 in which said composite has a Young's modulus from 2 GPa to 40 GPa.

13. A prosthesis according to claim 12 in which said composite has a Young's modulus from 5 GPa to 30 GPa.

14. A prosthesis according to claim 2 in which said composite has been oriented in a machine direction.

15. A prosthesis according to claim 14 wherein the ratio $E_{||}:E_{\perp}$ of said composite is from 1 to 3.

16. A prosthesis according to claim 12 which is a femoral prosthesis.

17. A prosthesis for replacement of bone according to claim 16 with 35 to 45 percent by volume of a particulate calcium phosphate filler.

18. A prosthesis for replacement of bone comprising a composite formed by compounding, in the solid phase, a homo- or copolyolefin having a weight average molecular weight ($M_w$) greater than 100,000 with from 30 to 50 percent by volume of a particulate calcium salt wherein the calcium salt is a natural or synthetic hydroxyapatite or fluorapatite having a Ca:P ratio from 1.51 to 1.7, said composite having a Young's modulus in the range of values recorded for compact bone.

19. An artificial hip comprising a composite formed by compounding, in the solid phase, a homo- or copolyolefin having a weight average molecular weight ($M_w$) greater than 100,000 with from 30 to 50 percent by volume of a particulate calcium phosphate, said composite having a Young's modulus in the range of values recorded for compact bone.

* * * * *

UNITED STATES PATENT AND TRADEMARK OFFICE
CERTIFICATE OF CORRECTION

PATENT NO. : 5,017,627

DATED : May 21, 1991

INVENTOR(S) : Bonfield et al.

It is certified that error appears in the above-identified patent and that said Letters Patent is hereby corrected as shown below:

Claim 16, Col. 6, line 36, delete "claim 12" and insert --claim 1--.

Claim 17, Col. 6, line 39, delete "claim 16" and insert --claim 1--.

Signed and Sealed this

Twenty-ninth Day of September, 1992

Attest:

DOUGLAS B. COMER

*Attesting Officer*   *Acting Commissioner of Patents and Trademarks*